United States Patent
Goldmann et al.

(10) Patent No.: US 8,728,152 B2
(45) Date of Patent: May 20, 2014

(54) WOVEN AORTIC SINUS PROSTHESIS HAVING A BULB

(75) Inventors: Helmut Goldmann, Tuttlingen/Donau (DE); Christof Merckle, Mannheim (DE); Hans-Hinrich Sievers, Kronshagen (DE)

(73) Assignee: Aesculap AG (DE)

(*) Notice: Subject to any disclaimer, the term of this patent is extended or adjusted under 35 U.S.C. 154(b) by 803 days.

(21) Appl. No.: 12/520,284

(22) PCT Filed: Oct. 19, 2007

(86) PCT No.: PCT/EP2007/009080
§ 371 (c)(1),
(2), (4) Date: Aug. 26, 2009

(87) PCT Pub. No.: WO2008/083767
PCT Pub. Date: Jul. 17, 2008

(65) Prior Publication Data
US 2010/0094390 A1    Apr. 15, 2010

(30) Foreign Application Priority Data
Dec. 22, 2006   (DE) .......................... 10 2006 062 360
Mar. 13, 2007   (DE) .......................... 10 2007 013 428

(51) Int. Cl.
*A61F 2/06* (2013.01)
(52) U.S. Cl.
CPC ........... *A61F 2/06* (2013.01); *A61F 2250/0017* (2013.01); *A61F 2250/0039* (2013.01)
USPC ........................................ 623/1.51; 623/1.3

(58) Field of Classification Search
CPC ... A61F 2/06; A61F 2/2451; A61F 2002/068; A61F 2/2475; A61F 2002/30914; A61F 2250/0017; A61F 2250/0028; A61F 2250/0039
USPC ............... 623/1.51–1.53, 1.5, 1.54, 1.3, 1.35, 623/1.13, 1.23, 1.28, 1.29
See application file for complete search history.

(56) References Cited

U.S. PATENT DOCUMENTS

| 5,139,515 A | 8/1992 | Robicsek |
| 5,662,675 A | 9/1997 | Stockert et al. |

(Continued)

FOREIGN PATENT DOCUMENTS

| CN | 1522675 A | 8/2004 |
| DE | 101 62 821 A1 | 6/2003 |

(Continued)

OTHER PUBLICATIONS

Anderson, K., "Seamless Textiles with Inherent Shape," *North Carolina State University*, 2004, Thesis, cover page, index through p. 228.

(Continued)

*Primary Examiner* — David Isabella
*Assistant Examiner* — Suba Ganesan
(74) *Attorney, Agent, or Firm* — DLA Piper LLP (US)

(57) ABSTRACT

A woven aortic sinus prosthesis has a first substantially cylindrical section position away from a patient's heart, which optionally passes into an aortic arch of the patient, a second section having a greater diameter than the first section and forming a bulb, which second section is connected to the first section, and optionally a third substantially cylindrical section close to the heart, which is connected to the bulb section, wherein the prosthesis is continuously woven and has a constant number of warp yarns over its axial length, whereby there is a greater distance between the warp yarns in a region of the bulb section than in the first and third cylindrical sections.

28 Claims, 3 Drawing Sheets

(56) References Cited

U.S. PATENT DOCUMENTS

| | | |
|---|---|---|
| 6,454,796 B1 | 9/2002 | Barkman et al. |
| 6,544,285 B1 | 4/2003 | Thubrikar et al. |
| 6,575,201 B2 | 6/2003 | Buesgen |
| 7,465,316 B2 * | 12/2008 | Kujawski ............... 623/1.31 |
| 7,758,633 B2 * | 7/2010 | Nazzaro ................. 623/1.3 |
| 7,833,263 B2 * | 11/2010 | Thistle .................. 623/1.32 |
| 2002/0052649 A1 * | 5/2002 | Greenhalgh ............ 623/1.35 |
| 2003/0078650 A1 | 4/2003 | Nunez et al. |
| 2003/0196717 A1 | 10/2003 | Nunez et al. |
| 2005/0070994 A1 | 3/2005 | Sievers et al. |
| 2005/0240261 A1 | 10/2005 | Rakos et al. |

FOREIGN PATENT DOCUMENTS

| | | |
|---|---|---|
| DE | 102 42 154 A1 | 3/2004 |
| DE | 697 28 268 T2 | 1/2005 |
| EP | 0 955 019 A2 | 11/1999 |
| JP | 03-045743 A | 2/1991 |
| JP | H10-168701 | 6/1998 |
| JP | 2001-525017 | 12/2001 |
| JP | 2002-17758 | 1/2002 |
| WO | 99/40875 A1 | 8/1999 |
| WO | 01/52776 A1 | 7/2001 |
| WO | 03/090643 A1 | 11/2003 |
| WO | 2004/021925 A2 | 3/2004 |
| WO | 2005/099624 A1 | 10/2005 |
| WO | 2005/099634 A1 | 10/2005 |

OTHER PUBLICATIONS

Anderson, K. et al., "Developing Seamless Shaped Woven Medical Products," *Journal of Medical Engineering & Technology*, May/Jun. 2004, vol. 28, No. 3, pp. 110-116.

Anderson, K., "Seamless Textiles with Inherent Shape," *North Carolina State University*, Jul. 2005, Dissertation, Abstract only (3 pages).

* cited by examiner

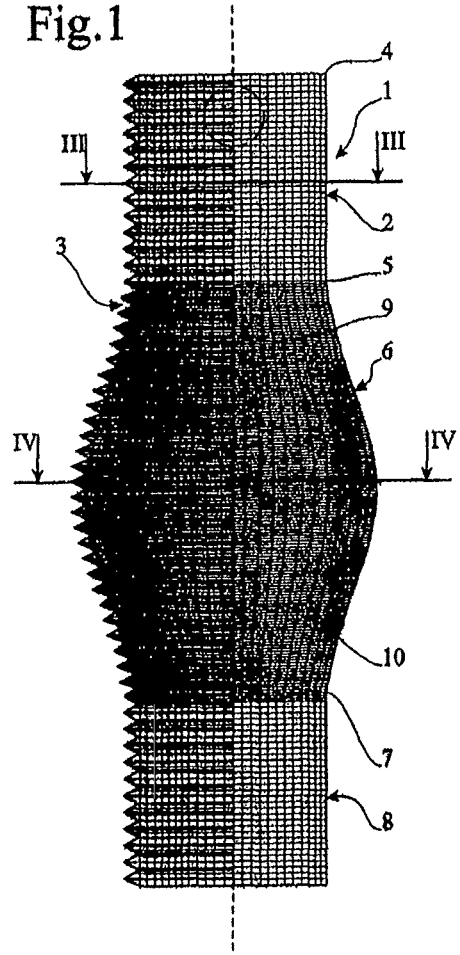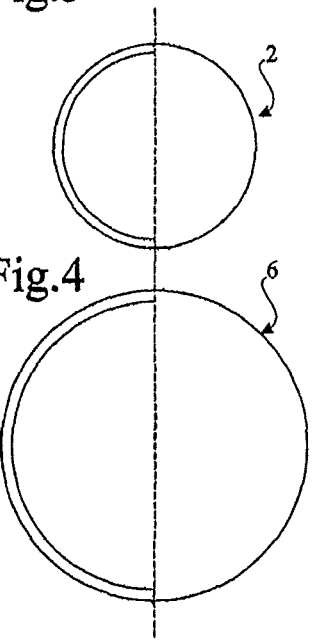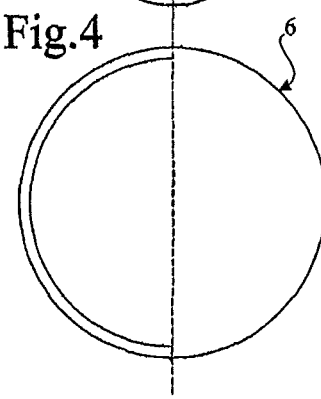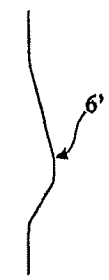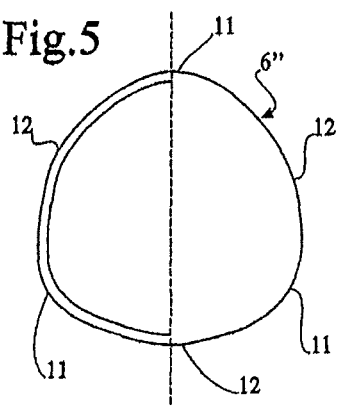

WOVEN AORTIC SINUS PROSTHESIS HAVING A BULB

RELATED APPLICATIONS

This is a §371 of International Application No. PCT/EP2007/009080, with an international filing date of Oct. 19, 2007 (WO 2008/083767 A1, published Jul. 17, 2008), which is based on German Patent Application Nos. 10 2006 062 360.6, filed Dec. 22, 2006, and 10 2007 013 428.4, filed Mar. 13, 2007.

TECHNICAL FIELD

This disclosure concerns a woven aortic sinus prosthesis.

BACKGROUND

The replacement of areas of the aorta close to the heart, particularly the so-called "ascending aorta," is one of the most important specialties of modern heart surgery. A number of vascular prostheses are now available for doing this. The vascular prostheses are usually implanted after removal of the aneurysmatic sections of the ascending aorta and, particularly, after removal of the aortic sinus (natural sinus) while retaining the aortic valves and sections of the arterial wall.

The early vascular prostheses were straight and homogeneous tubular prostheses. The disadvantage of these types of vascular prostheses is that they do not have the additional structures which could replace the functions of the surgically removed aortic sinus in particular. Consequently, they do not conform adequately to the actual anatomical conditions of the ascending aorta.

Tubular vascular prostheses for replacing the ascending aorta are known from U.S. Pat. No. 6,544,285 B1 and WO 01/52776 A1, which have artificial sinuses in the area close to the heart for replacing the aortic sinuses. The artificial sinuses are sewn to the prosthesis. Arched bulges are formed at the end close to the heart of the vascular prosthesis by the sewn-on sinuses. Basically, these vascular prostheses do improve the conformation to the actual anatomical conditions of the ascending aorta, but it is much more difficult to implant them.

EP 0 955 019 A2 concerns tubular vascular prostheses having a generally circumferential bulge in the region of the aortic bulb. Even this prosthesis configuration does not correspond to the actual anatomy of the ascending aorta. WO 2004/021925 A2 describes a tubular vascular prosthesis that has been improved in this respect, whereby the tubes in the region of the ascending aorta have at least two artificial sinuses, which have a greater external dimension than the tubes themselves. Furthermore, U.S. Pat. No. 5,139,515 describes an aortic prosthesis having sinus-like bulges, but does not give any more details on the formation of the bulges. WO 2005/099624 A1 describes a woven aortic sinus prosthesis having a substantially spherical bulb section. A complicated weaving technique is required to produce it.

It could therefore be helpful to provide a vascular prosthesis for replacing the ascending aorta which is easy to produce and which avoids the known disadvantages of the prior art, and which particularly has a configuration which satisfactorily conforms to the natural anatomical conditions of the ascending aorta.

SUMMARY

We provide a woven aortic sinus prosthesis including a first substantially cylindrical section position away from a patient's heart, which optionally passes into an aortic arch of the patient, a second section having a greater diameter than the first section and forming a bulb, which second section is connected to the first section, and optionally a third substantially cylindrical section close to the heart, which is connected to the bulb section, wherein the prosthesis is continuously woven and has a constant number of warp yarns over its axial length, whereby there is a greater distance between the warp yarns in a region of the bulb section than in the first and third cylindrical sections.

BRIEF DESCRIPTION OF THE DRAWINGS

Further characteristics and features are given in the following description of representative examples of methods of manufacture. In this case, the individual features may be realized in their own rights, or else in combination with each other. The examples only serve as an explanation and are not limited to it in any way.

FIG. 1 is a side view of an aortic sinus prosthesis;

FIG. 2 is a view from above of the outer, right-side warp yarn of an alternative to the prosthesis shown in FIG. 1;

FIG. 3 is a cross section taken along line III-III according to FIG. 1;

FIG. 4 is a cross section taken along line IV-IV according to FIG. 1;

FIG. 5 is a cross section of an irregularly extended bulb section;

DETAILED DESCRIPTION

Figure 6:
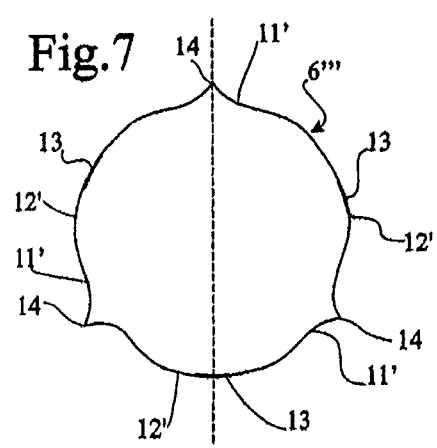
FIG. 6 is a side view of another prosthesis.

We provide a woven aortic sinus prosthesis having a first, substantially cylindrical, section not close to the heart, which may possibly pass into an aortic arch, a second section having a greater diameter than the first section and forming a bulb (bulge), which second section is connected to the first section, and possibly a third, substantially cylindrical, section close to the heart, which is connected to the bulb. The aortic sinus prosthesis may be continuously woven and has a constant number of warp yarns over its axial length, whereby there is a greater distance between the warp yarns in the region of the bulb section than in the cylindrical regions of the prosthesis.

We provide for an aortic sinus prosthesis which is particularly suitable for replacing the ascending aorta. Thanks to the bulb-shaped second section, the prosthesis largely corresponds to the anatomical conditions of the natural aorta, particularly with regard to the natural sinuses. Consequently, following implantation of the aortic sinus prosthesis, the bulb can fill with blood during systole, and this is pumped onwards during diastole, thanks to the preferably elastic properties of the prosthesis.

The bulb section may have a maximum diameter, which is about 1 to about 45%, preferably about 10 to about 40%, particularly about 15 to about 35%, greater than the diameter of the cylindrical sections of the aortic sinus prosthesis. In special cases, the bulb diameter may be up to about 50% greater than the diameter of the cylindrical section. The aortic sinus prosthesis normally has a diameter of about 24 to about 40 mm in the cylindrical regions, and usually about 28 to about 32 mm. In the bulb section, the maximum diameter is normally about 30 to about 50 mm, usually a maximum of about 32 to about 48 mm, and particularly a maximum of about 34 to about 38 mm.

The first cylindrical section not close to the heart preferably has a length of about 20 to about 150 mm, particularly about 50 to about 100 mm, and up to about 200 mm in special cases. The bulb preferably has an axial length of about 20 to about 50 mm, particularly about 25 to about 30 mm, and up to about 60 mm in special cases.

A third, substantially cylindrical section of the prosthesis close to the heart has an axial length of about 5 to about 30 mm, particularly about 10 to about 20 mm. In this structure, the vascular prosthesis is also suitable for replacing the ascending aorta and remodeling the aortic sinus root (annulus).

The bulb section preferably has three longitudinal sub-sections in the axial direction, in which the distance between the warp yarns of a first sub-section not close to the heart increases constantly, particularly continuously, a second central sub-section, in which the distance between the warp yarns is substantially constant, and a third sub-section close to the heart, in which the distance between the warp yarns tapers substantially constantly to the diameter of the cylindrical section of the prosthesis. The bulb section may have two longitudinal sub-sections in the axial direction, whereby a second sub-section close to the heart, having a constantly tapering warp yarn spacing, is connected directly to a first sub-section not close to the heart having a constantly, particularly continuously, increasing warp yarn spacing. We particularly provide for the three or two bulb sub-sections having different lengths in the axial direction.

In a further structure, the first bulb sub-section is at least the same length as a third sub-section. The first bulb sub-section is preferably longer than a third section. In this case, the increase in diameter of the first section is correspondingly more gradual. The same applies to the taper of the first section in this case.

In one example, the warp yarns in the bulb section, when looked at in the circumferential direction, are slightly opened out, so that a bulb extending uniformly over the entire circumference is produced. In another example, the distances between the warp yarns may vary in the cross section of the bulb section. Consequently, in one example, the bulb section may have three individual bulbs, which are formed by three circumferential regions having increased warp yarn spacings. The warp yarn spacing between the individual bulbs may either be the same as in the cylindrical sections of the prosthesis or the spacings may be wider, but they are smaller than in the bulges of the individual bulbs. The increase in spacing may be such that the bulb section or the individual bulbs are divided into individual sub-sections, or have a uniform balloon-shaped transition.

Basically, every type of natural and/or synthetic fiber may be used as materials for producing the woven aortic sinus prosthesis. The fibers may be single or multifilament types. Preferably the yarns are continuous yarns. The yarns are expediently made from a biocompatible material. Polyester, particularly polyethyleneterephthalate, is a non-limiting example of a preferred yarn material.

The aortic sinus prosthesis may have a water-permeability value in the region of 0 to about 500 ml/cm$^2$, particularly in the region of about 200 to about 250 ml/cm$^2$. These water-permeability values were measured at 120 mmHg according to Wesolowski's method. The aortic sinus prosthesis is therefore blood-tight after a short time and the risk of blood seepage is low.

The woven fabric of the aortic sinus prosthesis particularly has a thickness of about 0.1 to about 0.35 mm, preferably about 0.15 to about 0.25 mm. The thickness is determined according to DIN 863.

The woven fabric is preferably made from yarns having a count of about 10 to about 200 dtex. The yarns may have a twist value of about 50 to about 500 turns/m, for example. The yarns in the woven aortic sinus prosthesis may also comprise particularly about 10 to about 200 filaments, particularly about 20 to about 150 filaments, preferably about 80 filaments per yarn. The woven fabric may have a repeat of 8×8.

The density of the warp yarns in the cylindrical section of the prosthesis may be about 30 to about 120 yarns per cm of the prosthesis circumference, particularly about 40 to about 80 yarns per cm of the prosthesis circumference. The density of the filling yarns in the cylindrical section of the prosthesis may preferably be about 10 to about 70 yarns per cm of the prosthesis length, particularly about 20 to about 50 yarns per cm of the prosthesis length.

In one example, the first section not close to the heart and the third section close to the heart have different internal diameters, together with a correspondingly different warp yarn spacing. The third section close to the heart preferably has a greater internal diameter. The internal diameters of vascular prostheses usually increase uniformly by about 2 mm in each case in ascending order of prosthesis size. The difference in the diameters between the third and the first section is also preferably about 2 mm in each case.

Depending on the anatomical conditions, the third section close to the heart may also have a smaller internal diameter than the first section not close to the hear, so that the relationships are reversed. It is also possible to form the first and/or third sections so that they are slightly tapered.

Basically, the standard constructions for woven fabrics can be used to produce the aortic sinus prosthesis. Preferably, the aortic sinus prosthesis is substantially a plain weave. In particular, the aortic sinus prosthesis may comprise a scaffold with a plain weave construction.

Preferably, untexturized yarns are used exclusively as the warp yarns. In one example, the warp yarns are exclusively texturized yarns. It is beneficial for the woven fabric to be made from a combination of untexturized and texturized yarns. For example, the overall ratio of untexturized to texturized yarns may be 1:1 to 6:1, particularly 3:1. In a particularly preferred example, the woven fabric of the aortic sinus prosthesis comprises at least about 50% untexturized yarns, i.e., yarns that have not been texturized.

Untexturized and texturized yarns may be used particularly in an alternating arrangement as the warp yarns, whereby the ratio of untexturized to texturized yarns is in a ratio of between 2:1 and 1:2, particularly approximately 1:1.

In a further example, the filling yarns may be untexturized or texturized. The filling yarns are preferably untexturized yarns. In another example, untexturized and texturized yarns may be used in an alternating arrangement in particular as the filling yarns, whereby the ratio of untexturized to texturized yarns is in the ratio of between 5:1 and 1:5.

The filling yarns may lie closer together in the region of the bulb than in the cylindrical region of the prosthesis. This means that the filling yarns in this section are preferably compacted.

It is beneficial to use shrinkable yarns, so-called "shrink yarns," as the filling yarns, at least for the section not close to the hear and preferably also for the section close to the heart. These preferably have an absolute shrinkability of at least about 20%, preferably a shrinkability that is at least about 30%, preferably at least about 40%, higher than the possible shrinkability of the filling yarns in the bulb, whereby the shrinkability is related to non-shrinkable yarns (0%). The difference in diameter between the substantially cylindrical sections and the bulb section can, therefore, be at least partly realized by the different shrinking values of the filling yarns. The differences in diameter between the substantially cylindrical sections, within these sections, and within the bulb can also be maintained.

Figure 9:
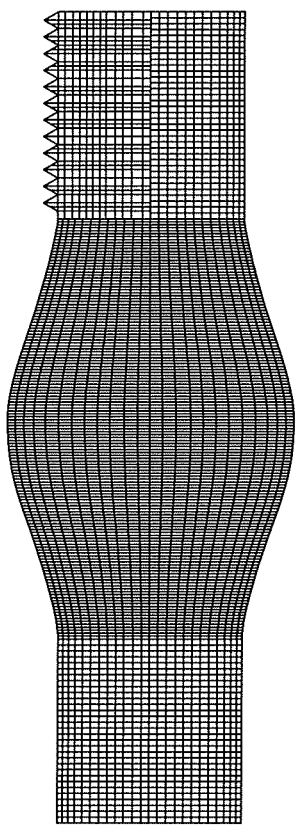
FIG. 9 is a side view of another prosthesis.

The aortic sinus prosthesis is preferably pleated, at least in the first cylindrical section of the prosthesis as shown in FIG. 9. It may also be pleated in the third cylindrical section of the prosthesis. The pleats should preferably run in the transverse direction.

It is especially beneficial for the aortic sinus prosthesis to be extensible in the region of the bulb section in the circumferential direction. The aortic sinus prosthesis preferably has pleats running in the longitudinal direction of the bulb region. The compliance (stretchability) of the aortic sinus prosthesis can thus be improved further. The pleated folds running in the longitudinal direction of the pleats may be thermally embossed (fixed), particularly towards the outside.

Float yarns may be used, particularly float yarns running in the warp direction. One of these float yarns is preferably located in addition to, and particularly parallel to, a warp yarn in the plain weave. The additional float yarn preferably runs with the parallel warp yarn in the plain weave construction and meets up again with the warp yarn after floating. The float yarns may lie flat in the woven fabric, particularly without forming loops. It is particularly beneficial for the float yarns to be texturized. In a preferred example, a floating texturized yarn lies adjacent to two untexturized yarns running in the same direction in the woven fabric construction.

In a further example, the woven fabric of the aortic sinus prosthesis may only comprise untexturized yarns, with a float formed from texturized yarns. In another example, the woven fabric may comprise alternating untexturized and texturized yarns, with a float made from texturized yarns, whereby, in particular, only every second texturized yarn has a float.

The float yarns preferably only run in the warp direction. However, the float yarns may run in both the warp and weft directions. A different number of float yarns may be incorporated in the warp and weft directions in particular.

Figure 8:
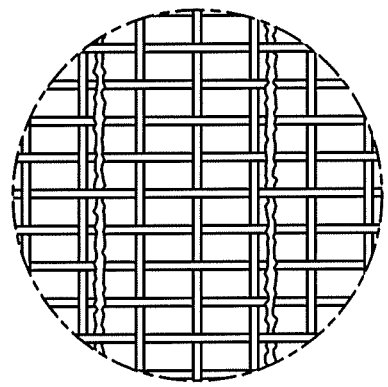
FIG. 8 is a view of a weave pattern with floats.

It is also preferably for the floats to run over more than 2 yarns, particularly over 3 to 10 yarns, preferably over 4 to 6 yarns. It is beneficial for the float to be incorporated 4 to 6 over 1, preferably 4 over 2, or 5 over 1. In a preferred example, a float may be incorporated over 5, under 1, over 1, under 1 for a repeat of 8×8. An odd number of floats is preferred, since other-wise the float yarns would no longer lie parallel to an adjacent weaving yarn in a plain weave construction. FIG. 8 shows a weave pattern with float yarns.

The ratio of float yarns to warp yarns may be between 1:20 to 1:1, particularly between 1:10 to 1:2, preferably 1:3. In other words, the float yarns may represent a percentage of roughly about 5 to about 50%, particularly from about 9 to about 33%, preferably about 25% in relation to the percentage of warp yarns in the woven fabric. The floats of adjacent float yarns in the warp direction may preferably by staggered, whereby preferably at least some of the floats overlap.

It is beneficial for the distance between the float yarns in the weft direction to be the same. In particular, at least three yarns may lie between them in the basic fabric. A maximum of two overlapping warp yarns may lie next to each other in the weft direction.

In the aortic sinus prosthesis, the float yarns may float only on one surface. The woven fabric construction preferably has floats on the outer side of the aortic sinus prosthesis, which are made from texturized yarns in particular. This enables fibroblasts to grow into the outer side of the aortic sinus prosthesis from the surrounding tissue and form the collagen for external encapsulation of the prosthesis.

The inner side of the prosthesis is preferably free of floats. It is particularly beneficial for the inner side of the aortic sinus prosthesis to have a smoother surface than the outer side. This may particularly favor the ingrowth of neointima. Consequently, the mesothelial cells can form a new thin smooth neointima starting from the vascular stumps.

A smooth inner surface is produced by pulling on the untexturized yarns more firmly to form the inner surface of the aortic sinus prosthesis. On the other hand, by preferably pulling on the texturized yarns more firmly to form the outer side of the aortic sinus prosthesis, an outer side is produced which has a voluminous structure compared to the inner side. This more structured outer surface means that a porosity gradient is maintained towards the inner surface of the aortic sinus prosthesis, whereby the ingrowth of blood vessels is improved and, at the same time, formation of the neointima is favored.

The aortic sinus prosthesis may be impregnated with a sealing agent. Resorbable materials are preferably used in the impregnation process. For example, gelatin and other suitable natural or synthetic materials may be considered as the impregnating agents. It is particularly beneficial for the impregnating agents to be crosslinked after the aortic sinus prosthesis has been coated.

The aortic sinus prosthesis is preferably free of joining seams.

The bulb may have several, particularly three, reinforcing elements running longitudinally in the wall of the bulb. The reinforcing elements may particularly be made from a prosthesis material, plastics or metals. For example, the reinforcing elements may be a gathered prosthesis material. Furthermore, the reinforcing elements may be formed from an additional prosthesis material, which may be sewn onto the aortic sinus prosthesis, for example. The reinforcing elements are preferably in the shape of a rib or strip. It is particularly beneficial that the reinforcing elements enable the aortic sinus prosthesis to be fixed firmly during the implantation process, whereby the ribs—the so-called "commissures"—of the natural aortic wall are fixed to the reinforcing elements, particularly by sewing. The reinforcing elements are preferably formed as reinforcing seams 15, as shown by example in FIG. 6.

Furthermore, the aortic sinus prosthesis may be finished with medically active substances. These types of active substances may be antibiotics, antiseptics, clotting agents, growth promoters and similar agents in particular.

The aortic sinus prosthesis may be shrunk, particularly by heat setting. In particular, the texturized yarns may be opened by the shrinking process.

The aortic sinus prosthesis is preferably provided in a sterilized form, and particularly in a made-up form.

In the example shown in FIGS. 1, 3 and 4, a woven aortic sinus prosthesis 1 has a section 2 not close to the heart which, apart from the transverse pleats 3, is formed cylindrically. At its upper end 4, section 2 not close to the heart may pass seamlessly or by means of a transverse seam into an aortic arch, which is not shown in the diagram. At its lower end 5, section 2 of the aortic sinus prosthesis not close to the heart passes axially and seamlessly into a bulb section 6. When looked at in the circumferential direction, the bulb section 6 may be extended uniformly (FIG. 1 and FIG. 4) or non-uniformly (FIG. 5). The bulb section 6 also has transverse pleats 3. A substantially cylindrical section 8 close to the heart is also connected axially and seamlessly to the lower end 7 of the bulb section 6 which again, apart from the transverse pleats 3, is formed cylindrically. The transverse pleats 3 thus extend over the entire length of the aortic sinus prosthesis 1.

In the example shown in FIG. 1, the spacing of the warp yarns 9 in the bulb section 6 increases gradually and then decreases again to a greater degree than it does in the cylindrical sections 2 and 8. This produces a balloon-like bulb 6. Furthermore, in this embodiment, the filling yarns 10 in the bulb section 6 lie closer to each other than in the cylindrical regions of the aortic sinus prosthesis 1.

In bulb 6' of the example shown in FIG. 2, the increase in the distance between the warp yarns is uniform to start with, so that the diameter of the bulb increases linearly. The diameter then remains constant over a predetermined length and then changes linearly again but more steeply than during the increase. In the embodiment shown in FIG. 5, a bulb 6" has three circumferential sections 11, in which the warp yarn spacing is much greater, and three circumferential sections 12 lying in between, in which the warp yarn spacing is smaller. Three individual bulbs 11 are thus formed, or at least indicated.

The bulb section 6 may accommodate a natural or an artificial heart valve. The lower cylindrical section 8 may also be shortened or cut if required, depending on how much of the natural aortic body (annulus) remains during the implantation process.

In the example shown in FIG. 6, the three sections are formed so as to be substantially the same as in the example shown in FIG. 1. The corresponding reference numbers are therefore used. The difference from the example shown in FIG. 1 is that the section 8' close to the heart has a larger internal diameter than the first section 2 not close to the heart. The difference in diameter is preferably 2 mm. Consequently, when the first section not close to the heart has an internal diameter of 28 mm, for example, the internal diameter of the third section 8' close to the heart is 30 mm. The number of warp yarns again remains unchanged. Only the warp yarn spacing is greater in the third section close to the heart than in the first section not close to the heart. Also, with larger or smaller aortic sinus prostheses having larger or smaller internal diameters, the difference in diameter is preferably 2 mm approximately in both cases.

Example of a Method of Manufacture

A tubular prosthesis having a diameter of 28 mm is woven in a plain weave construction on a loom. The prosthesis produced in this way has a bulb (protrusion) having a diameter of approximately 32 mm over an axial length of approximately 30 mm. The prosthesis produced has a diameter of approximately 28 mm above and below the bulb. The prosthesis may be woven as a tube of any length, in which the bulb sections are repeated at specific intervals. The prosthesis blanks may be produced by cutting between the bulb sections. Filling yarns having different shrink values may be used to produce the prosthesis. Whereas filling yarns that are not shrinkable, or only slightly shrinkable, are used for the bulb, shrink yarns having a shrinkability of at least about 30% may be used for the substantially cylindrical sections. Such shrink yarns are known and may have a shrinkage of up to about 70%. By selecting the relevant shrink yarns, the differences in diameter of the prosthesis may be designed or enhanced so as to be gradual or abrupt. Shrinkage is realized in particular by subjecting the woven prosthesis to a thermal treatment.

Figure 7:
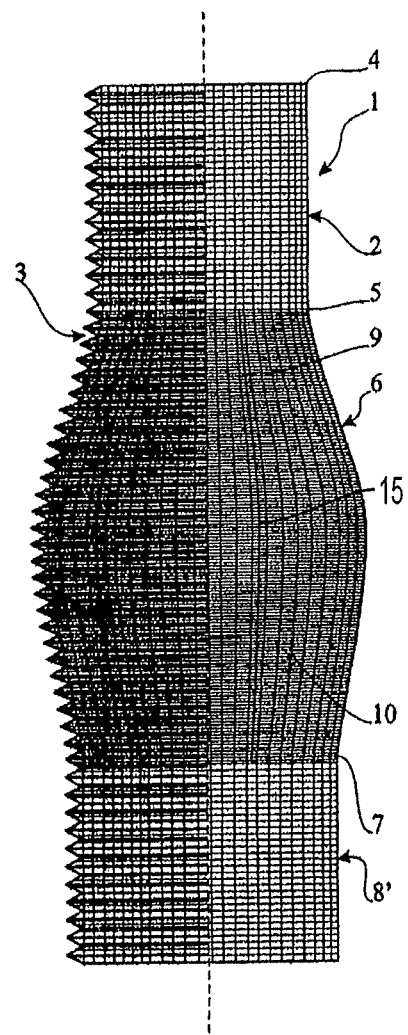
FIG. 7 is a cross section through a further prosthesis.

Following manufacture, the prosthesis blanks may be pleated above the bulb and below the bulb if necessary. The pleated sections are then cut to lengths of approximately 10 cm and approximately 3 cm. Three ribs 13 (FIG. 7) are then sewn at the same distance of approximately 3 mm apart from each other as reinforcing elements into the unpleated bulb by gathering the prosthesis material in the longitudinal direction of the prosthesis. After the reinforcing elements have been formed in the bulb region, the prosthesis is coated with gelatin. The gelatin is crosslinked. The prosthesis is finally subjected to a γ-sterilization process. In addition to, or instead of, the reinforcing elements 13, the prosthesis may be provided with longitudinal pleats in the bulb region. Three longitudinal pleated folds 14 are therefore provided in particular. It is beneficial for these to be in the form of three thermally fixed, outwardly running, longitudinal folds at the locations of the enlarged circumferential sections 11 (FIG. 5), as shown diagrammatically in FIG. 7. It is beneficial for three guidelines, staggered in relation to each other about an angle of 120° in the circumference, to be used as orientation lines instead of the usual two guidelines.

The invention claimed is:

1. A woven aortic sinus prosthesis comprising:
   first substantially cylindrical section positioned away from a patient's heart; and
   a second section having a greater diameter than the first section and forming a bulb, which second section is connected to the first section;
   wherein the prosthesis is continuously woven and has a constant number of warp yarns over its axial length, whereby 1) there is a greater distance between the warp yarns in a region of the bulb section than in the first section, 2) the bulb section includes three circumferential sections with larger warp yarn spacing alternating with three circumferential sections with smaller warp yarn spacing to create three individual bulbs, and 3) filling yarns lie closer together in the region of the bulb section than in the first cylindrical section.

2. The woven aortic sinus prosthesis as claimed in claim 1, wherein the bulb section has a maximum diameter which is about 1 to about 45% greater than a diameter of the first cylindrical section.

3. The woven aortic sinus prosthesis as claimed in claim 1, wherein the first cylindrical section has a length of about 20 to about 150 mm.

4. The woven aortic sinus prosthesis as claimed in claim 1, wherein the bulb section has an axial length of about 20 to about 50 mm.

5. The woven aortic sinus prosthesis as claimed in claim 1, wherein the bulb section has three longitudinal sub-sections in an axial direction in which the distance between the warp yarns of a first bulb sub-section, positioned away from the heart increases, a second central bulb sub-section, in which the distance between the warp yarns is substantially constant, and a third bulb sub-section adjacent the heart, in which the distance between the warp yarns constantly tapers up to the diameter of the cylindrical section of the prosthesis.

6. The woven aortic sinus prosthesis as claimed in claim 5, wherein the three bulb sub-sections have a different length in the axis direction.

7. The woven aortic sinus prosthesis as claimed in claim 5, wherein the first bulb sub-section is at least as long as the third sub-section.

8. The woven aortic sinus prosthesis as claimed in claim 5, wherein the first bulb sub-section is longer than the third sub-section.

9. The woven aortic sinus prosthesis as claimed in claim 1, wherein density of the warp yarns in the first cylindrical section is about 30 to about 120 yarns per cm of the prosthesis circumference.

10. The woven aortic sinus prosthesis as claimed in claim 1, wherein density of filling yarns in the first cylindrical section is about 10 to about 70 yarns per cm of the prosthesis length.

11. The woven aortic sinus prosthesis as claimed in claim 1, wherein the first section is produced using shrinkable filling yarns having a shrinkability of at least about 20%, and a difference in diameter compared to the bulb section is at least partly realized by shrinkage of these yarn.

12. The woven aortic sinus prosthesis as claimed in claim 1, wherein the shrinkability of the filling yarns in the first section is at least about 30% higher than shrinkability of the filling yarns used in the bulb region in relation to non-shrinkable yarns.

13. The woven aortic sinus prosthesis as claimed in claim 1, which is at least pleated in the first cylindrical section.

14. The woven aortic sinus prosthesis as claimed in claim 1, formed to be extensible in a circumferential direction in the region of the bulb section.

15. The woven aortic sinus prosthesis as claimed in claim 14, wherein pleated folds of pleats running in a longitudinal direction are formed by thermal embossing.

16. The woven aortic sinus prosthesis as claimed in claim 1, having floats on an outer side and being free of floats on an inner side of the prosthesis.

17. The woven aortic sinus prosthesis as claimed in claim 1, impregnated with a sealing agent.

18. The woven aortic sinus prosthesis as claimed in claim 1, which is free of joining seams.

19. The woven aortic sinus prosthesis as claimed in claim 1, wherein the bulb section has several reinforcing elements running longitudinally in a wall of the bulb section.

20. The woven aortic sinus prosthesis as claimed in claim 19, wherein the reinforcing elements are formed as reinforcing seams.

21. The woven aortic sinus prosthesis as claimed in claim 1, which is pleated only in the first cylindrical section of the prosthesis.

22. The woven aortic sinus prosthesis as claimed in claim 1, comprising pleats running in a longitudinal direction.

23. The woven aortic sinus prosthesis as claimed in claim 1, wherein the first substantially cylindrical section passes into an aortic arch of a patients heart.

24. The woven aortic sinus prosthesis as claimed in claim 1, further comprising a third substantially cylindrical section close to the heart.

25. The woven aortic sinus prosthesis as claimed in claim 24, wherein the third section is produced using shrinkable filling yarns having a shrinkability of at least about 20%, and a difference in diameter compared to the bulb section is at least partly realized by shrinkage of these yarns.

26. The woven aortic sinus prosthesis as claimed in claim 25, wherein the third section is at least about 30% higher than shrinkability of the filling yarns used in the bulb region in relation to non-shrinkable yarns.

27. The woven aortic sinus prosthesis as claimed in claim 24, wherein the third substantially cylindrical section has an axial length of about 5 to about 30 mm.

28. The woven aortic sinus prosthesis as claimed in claim 24, wherein the first section and the third section have different internal diameters and different warp yarn spacings, whereby the third section has a greater internal diameter than the first section.

* * * * *